United States Patent
Fischer et al.

(10) Patent No.: US 6,468,079 B1
(45) Date of Patent: Oct. 22, 2002

(54) ABRASIVE RADIOPAQUE ENDODONTIC MARKING TOOLS AND RELATED METHODS

(75) Inventors: Dan E. Fischer, Sandy, UT (US); Dan J. Bills, Sandy, UT (US)

(73) Assignee: Ultradent Products, Inc., South Jordan, UT (US)

(*) Notice: Subject to any disclaimer, the term of this patent is extended or adjusted under 35 U.S.C. 154(b) by 0 days.

(21) Appl. No.: 09/706,082

(22) Filed: Nov. 3, 2000

Related U.S. Application Data

(63) Continuation-in-part of application No. 09/356,636, filed on Jul. 19, 1999, now Pat. No. 6,155,825.

(51) Int. Cl.[7] .................................................. A61C 5/02
(52) U.S. Cl. ....................................................... 433/102
(58) Field of Search ........................... 433/102, 72, 75, 433/224, 165, 166, 81

(56) References Cited

U.S. PATENT DOCUMENTS

| | | | |
|---|---|---|---|
| 477,225 A | 6/1892 | Rauhe | 433/165 |
| 2,453,696 A | 11/1948 | Brooks | 433/165 |
| 3,330,040 A | 7/1967 | Kahn | 433/165 |
| 3,534,476 A | 10/1970 | Winters | 433/165 |
| 3,772,791 A | 11/1973 | Malmin | 433/224 |
| 4,190,958 A | 3/1980 | Martin et al. | 433/102 |
| 4,265,618 A | 5/1981 | Herskovitz et al. | 433/32 |
| 4,337,038 A | 6/1982 | Saito et al. | 433/32 |
| 4,571,180 A | 2/1986 | Kulick | 433/72 |
| 4,684,346 A | 8/1987 | Martin | 433/166 |
| 4,738,620 A | 4/1988 | Tomasini | 433/72 |
| 5,154,611 A | 10/1992 | Chen | 433/77 |
| 5,320,529 A | 6/1994 | Pompa | 433/76 |
| 5,464,362 A | 11/1995 | Heath et al. | 451/48 |
| 5,538,424 A | 7/1996 | Gelb | 433/72 |
| 5,558,652 A | 9/1996 | Henke | 604/280 |
| 5,807,106 A | 9/1998 | Heath | 433/102 |
| 6,093,157 A * | 7/2000 | Chandrasekaran | 600/585 |
| 6,238,491 B1 * | 5/2001 | Davidson et al. | 148/137 |

FOREIGN PATENT DOCUMENTS

| | | |
|---|---|---|
| CH | 392773 | 10/1965 |
| DE | 1294592 | 5/1969 |

* cited by examiner

*Primary Examiner*—Nicholas B. Lucchesi
*Assistant Examiner*—Melba Bumgarner
(74) *Attorney, Agent, or Firm*—Workman, Nydegger & Seeley

(57) ABSTRACT

Enhanced radiographic detection is provided by an endodontic marking instrument having a highly radiopaque elongate member, thereby enabling a dentist to better identify the location of the instrument in a root canal and the length of the root canal. The highly radiopaque, high contrast material of the elongate member is a non-toxic, material such as gold, platinum, palladium, silver, tungsten, and the like. The endodontic marking tools of the present invention are distinctly visible on radiographic images in light of the substantial contrast between the highly radiopaque material and the tooth of the patient.

28 Claims, 5 Drawing Sheets

ABRASIVE RADIOPAQUE ENDODONTIC MARKING TOOLS AND RELATED METHODS

RELATED APPLICATION

This application is a continuation-in-part of U.S. patent application Ser. No. 09/356,636 now as Pat. No. 6,155,825 which was filed on Jul. 19, 1999, and is entitled Radiopaque Endodontic Marking Tools and Related Methods. For purposes of disclosure of the present invention, the foregoing application is incorporated herein by specific reference.

BACKGROUND OF THE INVENTION

1. The Field of the Invention

This invention is in the field of instruments for use in medicine and dentistry. More specifically, this invention is in the field of endodontic instruments for treating root canals as part of a root canal procedure.

2. The Relevant Technology

To preserve a tooth that has a diseased pulp cavity, it is necessary to prevent bacterial proliferation within the pulp canal of the tooth by removing the diseased or necrotic pulp material from the pulp canal. After the pulp material has been removed or extirpated from a tooth, the pulp cavity is typically filled or obturated with a material such as gutta percha to occlude the pulp cavity and a sealer to seal the pulp cavity. This procedure is referred to as root canal therapy. Root canal cleaning is generally achieved by hand or mechanical instrumentation with files that are configured to bore and cut.

It is also common during the root canal procedure to irrigate a pulp cavity and the various root canals involved using an endodontic irrigator tip. Irrigation assists in removing debris and necrotic material cut by the endodontic files and bores. Disinfecting solutions can also be employed in irrigation, thereby disinfecting the pulp cavity and root canals during the operative procedure.

Root canals are often thin, tight, twisted and cumbersome to negotiate. A major problem associated with negotiating such awkward spaces during root canal therapy is apical perforation, i.e., perforation of the apex of the root canal. Another problem involves failing to clean material close enough to the apex, thus leaving necrotic tissue within the root canal. Before instrumentation of a root canal, the length of the root canal is determined to identify a suitable working length for the file or irrigation tip. Generally, the working length corresponds to the distance from a fixed reference position on the crown of a tooth to the apex.

Radiography is the most common method for measuring the length of the root canal. A preoperative x-ray image of the diseased tooth is taken from the front or back of the tooth, as depicted in FIG. 1, to show a cross-sectional view of the root canals 12 of tooth 10. The length of the root canal and the desired working length of the file or irrigation tip to be placed therein are then estimated.

Apical perforations typically result from an error in estimating the length of a root canal or the working length of the file or irrigation tip. Perforation of the apex 14 of a root canal 12 can result from the use of files or endodontic irrigation tips which are too long. Similarly, apex 14 can be perforated by extrusion of infected material through the apex due to the force exerted by the file or tip on the material as the file or tip is pushed downward to reach the apex. In addition to exposing the tissue surrounding the tooth to the infected material, apical perforations also substantially complicate subsequent healing of the root canal.

The possibility of perforating the apex is particularly frustrating because it is often desirable to deliver fluid which reaches the apex in order to disinfect the apex and dissolve necrotic tissue therein. However, certain fluids are too viscous to reach the apex if delivered too far above the apex or may entrap air, which prevents the fluid from reaching the apex.

Incomplete removal of necrotic material can thus result from the failure of a dental tool to reach far enough into a root canal. In light of the desire to maneuver dental tools close to the apex without perforating the apex, practitioners have followed up the initial radiographic procedure described above by placing a radiopaque instrument into the root canal of an opened tooth, then making a radiographic image of the root canal with the radiopaque instrument disposed therein, e.g., by taking an x-ray. This follow up procedure radiographically records the position of the tip of the instrument with respect to the apex of the root canal. Based on the x-ray with the tool in the root canal, the practitioner is able to adjust the penetrating length of a file or other tool.

The radiographic tools of the prior art have typically been the cutting tools, e.g., files, employed by the dentist during cleaning of the root canal. However, such typical cutting tools, particularly the smaller diameter tools, often yield a low contrast between the tools and the tooth in which the tools have been placed. Such radiographic tools are typically extremely thin, having a circumference measuring in the thousandths of inches in some circumstances. Consequently, it is often very difficult to clearly see and determine apex proximity of such typical radiographic tools on an x-ray image. Such low contrast tools typically comprise, for example, stainless steel or nickel-titanium as the radiographic material. Sonic techniques and electrical convective techniques can also be used in addition to radiographic techniques, but they are not always entirely accurate.

There is therefore a need within the art for an improved endodontic marking instrument and a method for using the instrument.

SUMMARY AND OBJECTS OF THE INVENTION

It is therefore an object of the invention to provide an improved endodontic tool and methods for making and using the tool.

It is another object of the invention to provide an improved endodontic marker.

It is another object of the invention to provide an endodontic marking tool which comprises a radiographic material having a high degree of contrast from the tooth of a patient.

In order to achieve the foregoing objects of the invention, endodontic marking tools comprising a highly radiopaque material are provided. The highly radiopaque material is a non-toxic, high contrast, material. The endodontic marking tools of the present invention show up significantly more clearly on radiographic images in light of the substantial contrast between the highly radiopaque material and the tooth of the patient. The radiopaque endodontic marking tools of the present invention are configured for placement within a root canal for detection by a radiographic instrument, such as an x-ray machine.

By way of example, the highly radiopaque material employed in the tools of the present invention may include a highly radiopaque material selected from the group consisting of gold, platinum, palladium, silver, and tungsten. Other embodiments further include an alloying agent.

A tool of the present invention comprises an elongate member having a distal insertion end and a proximal end. The elongate member has sufficient rigidity and ductility to be placed within and negotiate the angles of a root canal of a tooth such that the elongate member can be extended to a desired location within the root canal. The elongate member has a length and outer diameter that permits insertion of the elongate member into a root canal of a tooth.

The endodontic tool may have any suitable configuration which will permit insertion within a root canal. The shape of the tool may be cylindrical, tapered, or a variety of configurations. However, the endodontic tool is preferably configured for smooth insertion into the root canal without abrading capabilities. By way of example, such an endodontic tool may be a slender rod or wire. Such an endodontic tool is preferably used solely as a radiopaque marker. The endodontic tool may however also be configured as a cutting tool for abrasive cleaning such as an endodontic file or bit. Such an abrasive endodontic tool may also optionally be employed as a cutting tool prior to or following radiography.

These and other objects and features of the present invention will become more fully apparent from the following description and appended claims, or may be learned by the practice of the invention as set forth hereinafter.

BRIEF DESCRIPTION OF THE DRAWINGS

In order that the manner in which the above-recited and other advantages and objects of the invention are obtained, a more particular description of the invention briefly described above will be rendered by reference to a specific embodiment thereof which is illustrated in the appended drawings. Understanding that these drawings depict only a typical embodiment of the invention and are not therefore to be considered to be limiting of its scope, the invention will be described and explained with additional specificity and detail through the use of the accompanying drawings in which.

DETAILED DESCRIPTION OF THE PREFERRED EMBODIMENTS

FIGS. 2–5 depict various embodiments of endodontic marking tools respectively at 20, 30, 40 and 50. Each of these embodiments are sequentially discussed in detail. Reference is made primarily to the endodontic marking tool 20 depicted in FIG. 2 and shown being used in FIG. 6 in tooth 60, however, it should be understood that this is merely for illustrative purposes.

Figure 1:
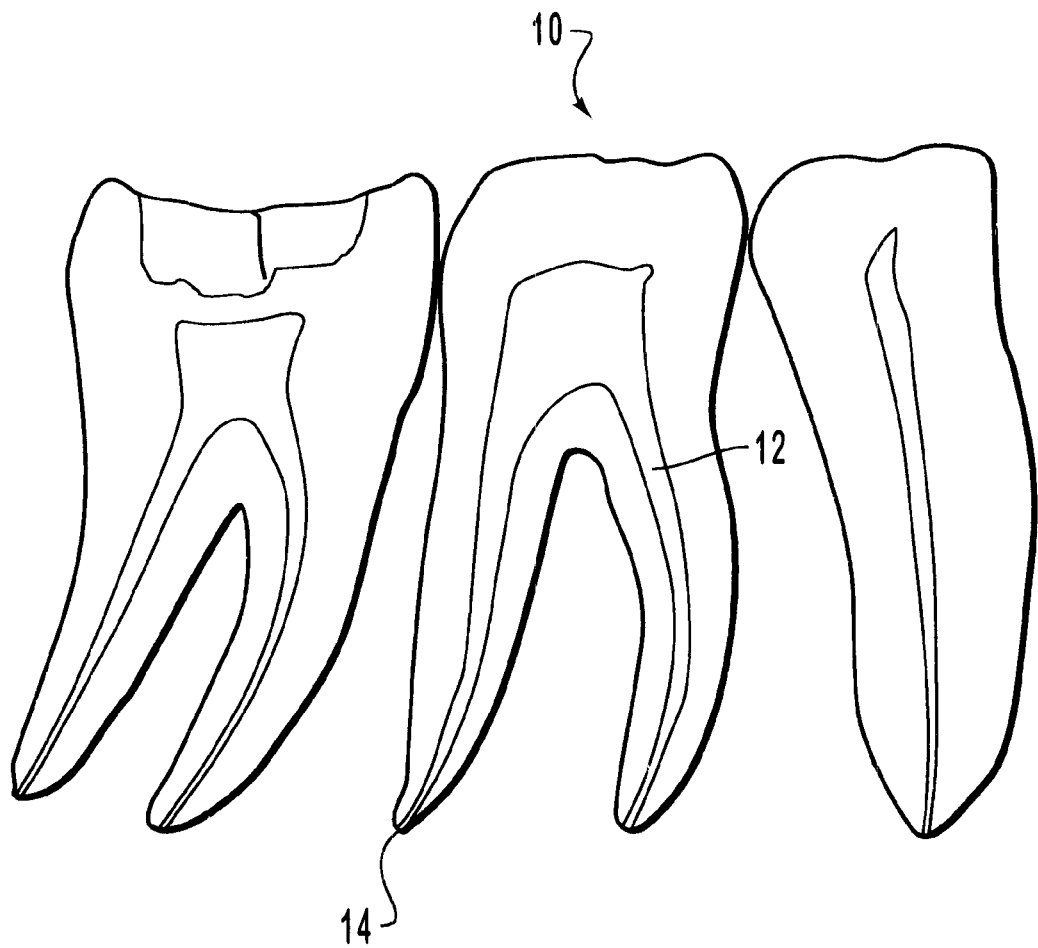
FIG. 1 is a depiction of a preoperative x-ray image of a series of diseased teeth taken in order to make an initial determination of the working length of an endodontic tool.
Figure 2:
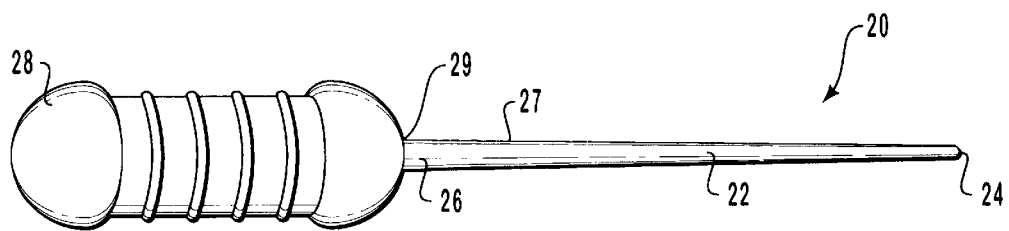
FIG. 2 is a top view of one embodiment of an endodontic marking tool 20 of the present invention.

With reference now to FIG. 2, tool 20 has an elongate member 22 with a distal insertion end 24 and a proximal end 26. Elongate member 22 extends from the distal stop end 29 of a handle 28. Stated otherwise, handle 28 partially ensheathes elongate member 22.

Elongate member 22 comprises a radiopaque material. The radiopaque material is preferably a "metallic material" which is understood, in the context of the present invention, to mean a metal, a material that includes a metal, or a combination of metals. The radiopaque material includes a "highly radiopaque material" that yields a desired radiopacity, as defined below. The highly radiopaque material provides a significantly higher radiographic contrast compared with metals conventionally utilized in endodontic radiography such as nickel titanium and stainless steel. As also explained below, the highly radiopaque material may be utilized in an essentially pure form, may be alloyed with other metals as long as the resulting alloyed metal has the desired radiopacity or may be a mixture such as a plastic containing particles of a highly radiopaque material.

Examples of materials which can be employed as highly radiopaque materials include gold, platinum, palladium, silver, tungsten, and the like, as these materials have a high contrast when exposed to x-rays or other radiographic equipment. In fact, they all have a mass x-ray absorption coefficient that is at least about 3.5. The resulting radiographic images show much higher contrast between the endodontic marking tool and the patient's tooth so that their position is very clear. This feature is of particular importance since the typical endodontic tools used often have a very small diameter, i.e., in the thousandths of inches in certain circumstances. These highly radiopaque materials are also nontoxic so they are safe for use within the oral cavity as radiopaque markers. They are also capable of being formed into tools which permit insertion into root canals.

Highly radiopaque materials include those that have a mass x-ray absorption coefficient that is at least about 2, preferably at least about 3 and more preferably about 3.5. In addition to gold, platinum, palladium, silver, and tungsten, there are many other materials that are also highly radiopaque materials such as iridium, osmium, rhenium, and rhodium; however, they are less preferred due to issues such as cost, availability, etc. Other materials such as lead and mercury are highly radiopaque, however, they are not particularly useful in dental applications in their pure forms due to their potential toxicity. The elements that have a mass x-ray absorption coefficient above 2 include those with the following atomic numbers: 32–35, 37–53, 55–83. The elements that have a mass x-ray absorption coefficient above 3 include those with the following atomic numbers: 37–53 and 55–83. Accordingly, the highly radiopaque material preferably includes elements other than noble gases that have an atomic number in the range of 32 to 83 and more preferably in the range of 37 to 83.

As noted above, the highly radiopaque material used in member 22 is a non-toxic material so that member 22 may be placed in the mouth of a patient. Since member 22 will likely encounter blood, saliva, water, endodontic pulp material and other fluid and cellular material, and should be sterile when used, the material employed in member 22 is also preferably autoclavable, corrosion resistant, and oxidation resistant. However, disposable embodiments are also available.

Member 22 is also rigid enough to be extended into a root canal, yet ductile or pliant enough to negotiate root canal areas. Furthermore, member 22 is configured with a length and outer diameter that permits insertion of elongate member 22 into a root canal of a tooth. The desired material for member 22 also has physical properties conducive to being formed into tools which permit insertion, yet negotiate the parameters of the root canal without breaking.

Gold, platinum, and palladium are autoclavable, corrosion resistant, and oxidation resistant. However, cost factors may suggest the use of tungsten, palladium or silver, rather than gold or platinum, in certain commercial settings.

If tungsten is utilized to form member 22, it is preferred to use high purity tungsten, such as a material with at least 99.9% W. This preferred composition provides member 22 with the necessary flexibility to negotiate the path of a root canal as member 22 is inserted therein, while member 22 is still stiff enough as to permit the effective insertion without impermissibly deforming member 22 as a consequence of engaging the walls or other features of a root canal. Tungsten is useful in the manufacture of member 22 due to its low cost relative to that of other highly radiopaque materials. Because of its low cost, tungsten radiopaque endodontic marking tools can be manufactured for single use applications. The disposable character of these tools reduces the number of instruments that are to be sterilized after each treatment. Silver may also be useful in the manufacture of a disposable embodiment due to its relative cost.

Figure 7:
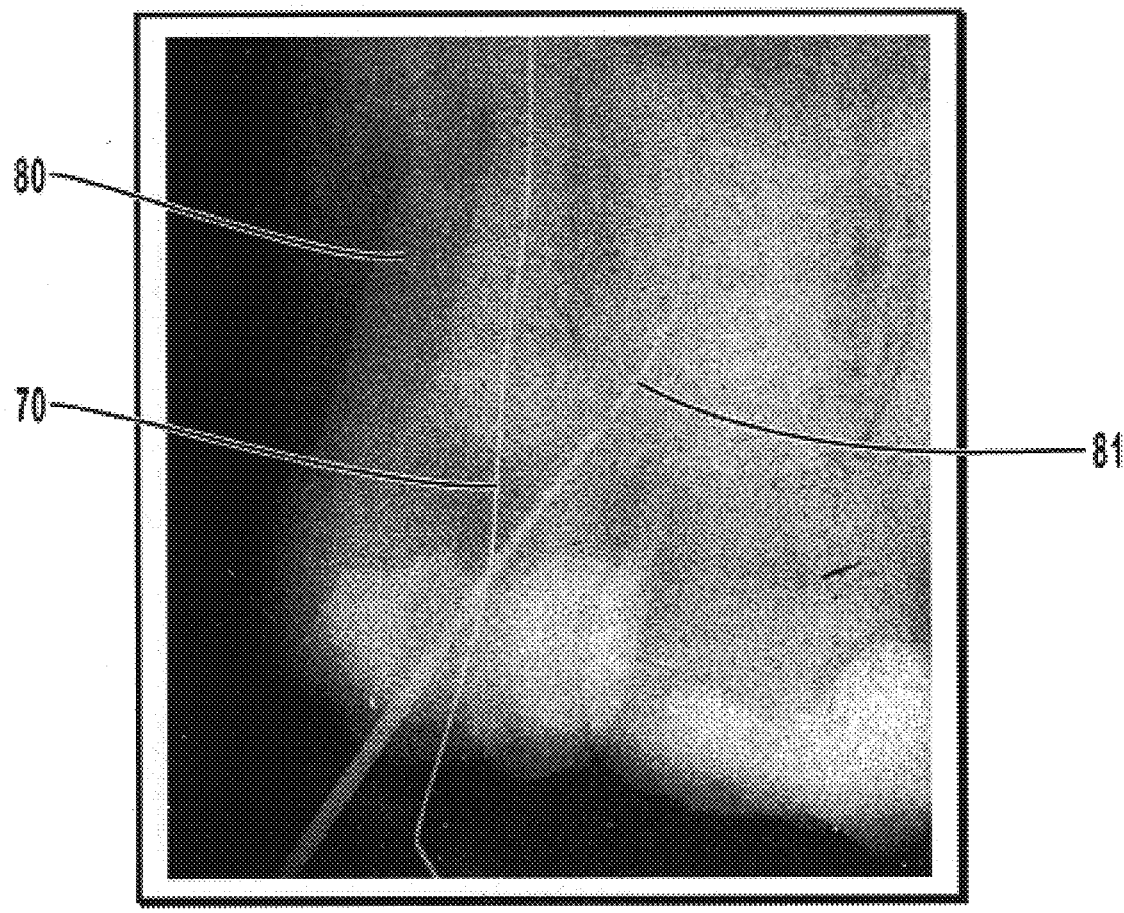
FIG. 7 is a negative radiographic image showing a conventional stainless steel endodontic file and an embodiment of the present invention.

FIG. 7 provides a qualitative distinction of the relative contrast achieved when using an elongate member formed from highly radiopaque material compared with materials typically used in endodontic radiography. More particularly, FIG. 7 is a negative radiographic image showing a generally cylindrical tungsten wire 70 in a tooth 80 as well as a stainless steel endodontic file 81. Tungsten wire 70 is radiographically visible by contrast over its entire length up to its distal insertion end 74 when exposed to Kα 0.2 Å x-rays from a tungsten source (W Kα 0.2 Å radiation). The diameter of wire 70 is about (1/6000)". In contrast, stainless steel endodontic file 81, also shown in the same radiograph, is generally not as highly contrasted as the tungsten wire and its distal insertion end 84 is hardly visible, thus rendering the task of reliably ascertaining the length of the working length difficult or even impossible.

The much higher contrast of tungsten wire 60 is particularly relevant because the diameter of this wire is equal to the diameter of stainless steel endodontic file 65 at its distal insertion end 67. In regions other than its distal insertion end, the diameter of stainless steel endodontic file 65 is greater than (1/6000)" because this file is tapered.

Figure 8:
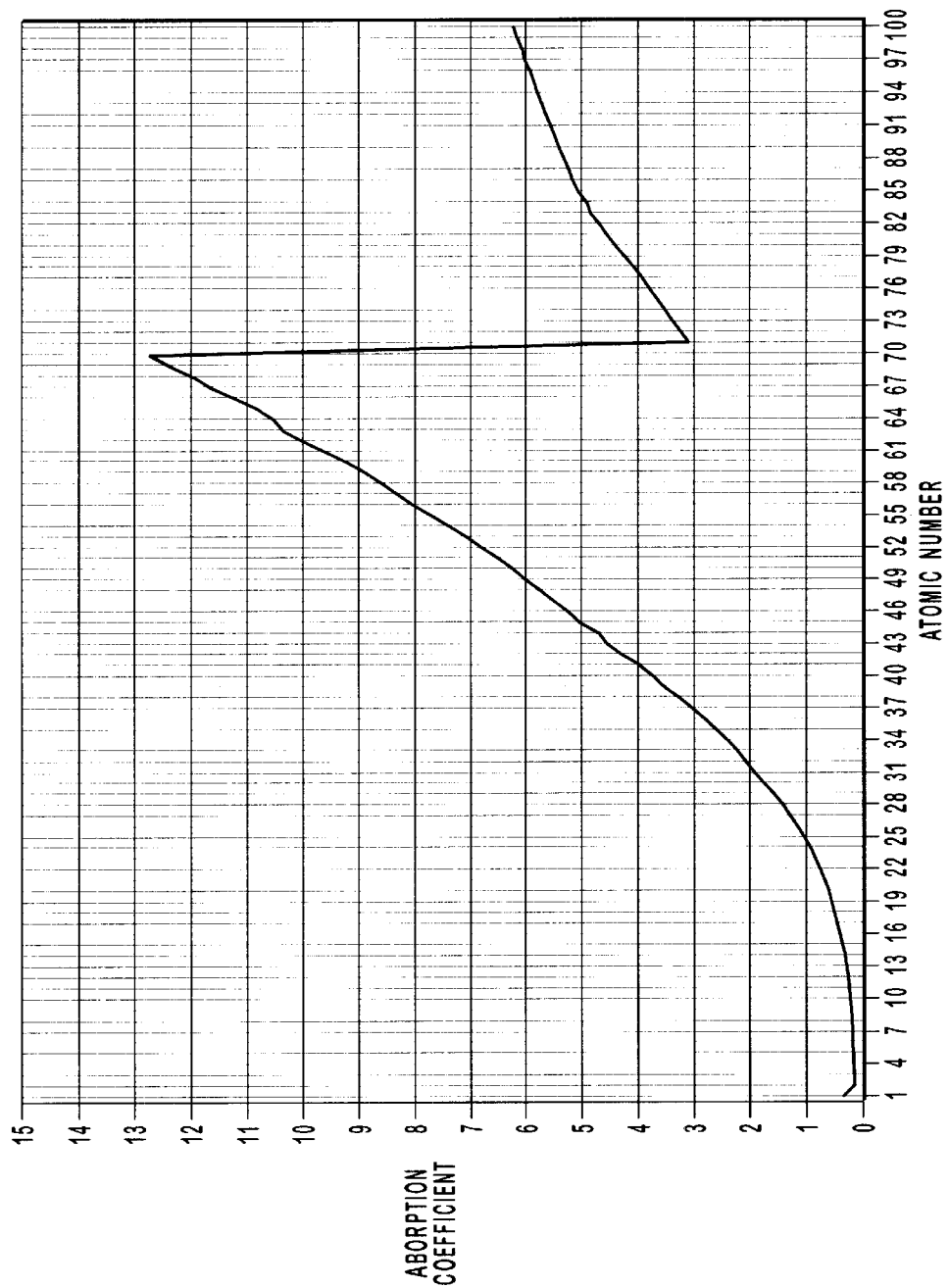
FIG. 8 provides a chart of the absorption coefficient for each element. The elements are identified by their respective atomic numbers.

To qualitatively describe the differences in contrast achieved when using the materials typically used in endodontic radiography, data is provided below that compares the mass x-ray absorption coefficients of materials such as stainless steel with the mass x-ray absorption coefficients of highly radiopaque materials used in the present invention. The data for two alloys that have relatively low radiopacity, nickel titanium and stainless steel, and their respective constituents is provided in Table 1A and Table 1B while the data for some highly radiopaque materials is provided in Table 2. FIG. 8 provides a chart of the absorption coefficient for each element wherein the elements are identified by their respective atomic numbers. The mass x-ray absorption coefficients are based on exposure of the element or alloy to Kα 0.2 Å x-rays from a tungsten source (W Kα 0.2 Å radiation). The data for the mass x-ray absorption coefficients was obtained from the HANDBOOK OF X-RAYS FOR DIFFRACTION, EMISSION, ABSORPTION AND MICROSCOPY by Emmett F. Kaelble, printed by McGraw-Hill and the INTERNATIONAL TABLES FOR X-RAY CRYSTALLOGRAPHY, VOLUME III from the INTERNATIONAL UNION OF CRYSTALLOGRAPHY, printed by D. Reidel Publishing (1983); both of which are incorporated by reference. The mass x-ray absorption coefficients for the low radiopacity alloys, nickel titanium and stainless steel, were calculated based on the data for their constituents using formulas provided below.

TABLE 1A

| Atomic Number | Element | Symbol | Molar Mass | Density g/ml | Mass x-ray Absorption Coefficient W Kα 0.2Å |
|---|---|---|---|---|---|
| | Nickel Titanium 55/45 | Ni—Ti | | 6.94 | 1.11 |
| 28 | Nickel | Ni | 58.700 | 8.90 | 1.42 |
| 22 | Titanium | Ti | 47.900 | 4.54 | 0.74 |

The data in Table 1A relates to a nickel titanium alloy made from 55% nickel and 45% titanium. Accordingly, the mass x-ray absorption coefficient for the alloy is approximately in between that of nickel and titanium.

TABLE 1B

| Atomic Number | Element | Symbol | Molar Mass | Density g/ml | Mass x-ray Absorption Coefficient W Kα 0.2Å |
|---|---|---|---|---|---|
| | 304 Stainless Steel | 304 SS | | 8.00 | 1.14 |
| 6 | Carbon | C | 12.011 | 2.10 | 0.17 |
| 14 | Silicon | Si | 28.086 | 2.33 | 0.31 |
| 24 | Chromium | Cr | 51.996 | 7.19 | 0.93 |
| 25 | Manganese | Mn | 54.938 | 7.20 | 1.03 |
| 26 | Iron | Fe | 55.847 | 7.87 | 1.16 |
| 28 | Nickel | Ni | 58.700 | 8.90 | 1.42 |

The data in Table 1B relates to stainless steel 304. Since stainless steel 304 is made primarily from iron, stainless steel 304 has a mass x-ray absorption coefficient that is only slightly less than that of iron. The remainder of the elements of stainless steel 304 include: 0.8% carbon, 1% silicon, 10–20% chromium, 8–10.5% nickel, and 2% manganese. Stainless steel 304 also typically contains negligible impurities such as 0.045% phosphorus and 0.03% sulfur.

TABLE 2

| Atomic Number | Element | Symbol | Molar Mass | Density g/ml | Mass x-ray Absorption Coefficient W Kα 0.2Å |
|---|---|---|---|---|---|
| 45 | Rhodium | Rh | 102.906 | 12.41 | 5.01 |
| 46 | Palladium | Pd | 106.400 | 12.02 | 5.25 |
| 47 | Silver | Ag | 107.868 | 10.50 | 5.50 |
| 56 | Barium | Ba | 137.34 | 3.6 | 7.98 |
| 74 | Tungsten | W | 183.850 | 19.30 | 3.50 |
| 75 | Rhenium | Re | 186.2 | 21.02 | 3.65 |
| 76 | Osmium | Os | 190.2 | 22.5 | 3.78 |
| 77 | Iridium | Ir | 192.22 | 22.65 | 3.92 |
| 78 | Platinum | Pt | 195.090 | 21.45 | 4.08 |

TABLE 2-continued

| Atomic Number | Element | Symbol | Molar Mass | Density g/ml | Mass x-ray Absorption Coefficient W Kα 0.2Å |
|---|---|---|---|---|---|
| 79 | Gold | Au | 196.967 | 19.30 | 4.22 |
| 82 | Lead | Pb | 207.200 | 11.35 | 4.67 |
| 83 | Bismuth | Bi | 208.980 | 9.8 | 4.81 |

As is evident from the data in Table 2 and from FIG. 8, the mass x-ray absorption coefficients for the preferred highly radiopaque materials, gold, platinum, palladium, silver, and tungsten, range from 3.5 to 5.5. These mass x-ray absorption coefficients are significantly higher than the mass x-ray absorption coefficients of the most commonly used materials in endodontics, nickel titanium and stainless steel, which have respective mass x-ray absorption coefficients of 1.14 and 1.11. Note that tungsten has a mass x-ray absorption coefficient of 3.5, which is the lowest of the preferred highly radiopaque materials, and yet the negative radiographic image provided in FIG. 7 clearly shows that the tungsten wire is significantly more visible than the stainless steel endodontic file. So the contrast provided by the other highly radiopaque materials is of course even greater than that of tungsten since they have mass x-ray absorption coefficients that are even higher.

In one embodiment, member 22 is formed from a pure, highly radiopaque material that is preferably a metal. However, the highly radiopaque materials may be used in alloy form to achieve some additional objective such as increased hardness, reduced cost or a desired rigidity and ductility for elongate member 22 to be inserted and moved within a root canal of a tooth. Thus, in another embodiment, member 22 is formed from an alloy of: (i) a highly radiopaque material that is a metal; and (ii) an alloying agent. So an alloyed material of the present invention for member 22 comprises: (i) a first element selected from the group consisting of gold, iridium, osmium, platinum, palladium, rhenium, rhodium, silver, tungsten, and the like, and (ii) an alloying agent, wherein the alloying agent is a second element which is different from the first element. The alloying agent may be either a highly radiopaque material or a low radiopacity material. Note that the term "low radiopacity material" as used herein includes any material that is not a highly radiopaque material such as a material which has a mass x-ray absorption coefficient that is lower than 2 or 1.5.

As is apparent from the foregoing discussion, a highly radiopaque material may serve as an alloying agent for another highly radiopaque material or an alloying agent may be selected which is not necessarily a highly radiopaque material. Thus, examples of alloying agents for gold include copper, chromium, iron, nickel, titanium, platinum, palladium, silver, tungsten, rhodium, iridium, osmium and ruthenium; examples of alloying agents for platinum include copper, chromium, iron, nickel, titanium, gold, palladium, silver, tungsten, rhodium, iridium, osmium and ruthenium; examples of alloying agents for palladium include copper, chromium, iron, nickel, titanium, gold, platinum, silver, tungsten, rhodium, iridium, osmium and ruthenium, and so on. The highly radiopaque material, such as gold, platinum, palladium, silver, and/or tungsten may also be alloyed with a low radiopacity alloyed material such as those used in manufacturing conventional endodontic instruments namely stainless steel or nickel-titanium.

Of course combining a highly radiopaque material with a low radiopacity material results in a radiopaque material with a lower mass x-ray absorption coefficient than the pure highly radiopaque material. As indicated above, this may be necessary in some circumstances to achieve other results such as greater hardness, greater flexibility or lower cost in addition to achieving sufficient radiopacity. Note that since endodontic radiography involves the use of conventional endodontic materials such as nickel titanium and stainless steel which have a mass x-ray absorption coefficient of about 1.1, use of even small amounts of a highly radiopaque material significantly increases the radiopacity compared with that of conventional instruments.

An elongate member configured to be inserted within a root canal of a tooth that is formed from a radiopaque material obtained by alloying, combining or mixing a highly radiopaque material with a low radiopacity material preferably has a mass x-ray absorption coefficient with respect to exposure to W Kα 0.2 Å radiation that is no less than about 1.5. Such a mass x-ray absorption coefficient is significantly higher than that of endodontic instruments conventionally used in endodontic radiography, namely nickel titanium and stainless steel. While member 22 may comprise a radiopaque material having a mass x-ray absorption coefficient that is no less than about 1.5, the mass x-ray absorption coefficient is preferably at least about 2, and more preferably at least about 3. Of course, the mass x-ray absorption coefficient of the radiopaque material or the elongate material formed therefrom may be much higher, depending on the concentration of the highly radiopaque material. Accordingly, the alloyed material may have a mass x-ray absorption coefficient of about 3.5, about 4, about 5, about 5.5, etc.

The mass x-ray absorption coefficients of an alloyed material formed from a highly radiopaque material and an alloying agent is determined by a simple mathematical operation. The mass x-ray absorption coefficient of an alloy is given by the weighted average of the mass x-ray absorption coefficients of the individual alloy constituents. For example, in an alloy with $c_1\%$ of constituent $m_1$ whose mass x-ray absorption coefficient is $x_1$, and $c_2\%$ of constituent $m_2$ whose mass x-ray absorption coefficient is $x_2$, the mass x-ray absorption coefficient of the alloy is given by $((c_1 \times x_1)+(c_2 \times x_2))/100$, where the composition is referred to mass. Accordingly, the composition of an alloy can be designed after a specific mass x-ray absorption coefficient has been selected.

The possible combinations of alloys are very numerous, however, several are included herein for purposes of illustration. For example, the elongate member of the dental tool may comprise an alloy of (i) a first highly radiopaque material such as gold, platinum, palladium, silver and/or tungsten; and (ii) copper, chromium, iron, nickel, titanium and/or a second highly radiopaque material other than the first highly radiopaque material. Examples of highly radiopaque materials which are usefully alloyed with each other include gold, platinum, and palladium. For example, gold and palladium may be combined. However, gold, platinum and/or palladium may be alloyed with many materials including silver, tungsten, rhodium, iridium, ruthenium, osmium, copper, chromium, iron, nickel, titanium, and other materials.

Examples of alloying agents which are particularly useful in conjunction with tungsten include copper and nickel. Tungsten and other materials described herein as being useful for member 22 may be plated with a material such as gold, palladium or platinum, for example, or with other suitable materials.

As indicated above, silver may be useful in the manufacture of a disposable tool. However, silver is preferably employed in an alloy form. Silver is an especially useful alloy due to its very high mass x-ray absorption coefficient, 5.5.

Although specific alloying agent are disclosed herein, including those selected from the group consisting of copper, chromium, iron, nickel, titanium, gold, platinum, palladium, silver, tungsten, rhenium, rhodium, iridium, ruthenium, and osmium, any suitable alloying agent may be utilized. More particularly, any suitable alloying agents may be used in combination with the highly radiopaque material to accomplish a particular objective such as desired rigidity and ductility of the elongate member as long as the elongate member has the desired mass x-ray absorption coefficient.

An example of an alloyed composition used to form member 22 includes a composition comprising (i) a highly radiopaque material in the range of about 0.1% by weight to about 99.9% by weight; and (ii) an alloying agent in the range of about 0.1% by weight to about 99.9% by weight. Another example of an alloyed composition includes a composition comprising (i) a highly radiopaque material in the range of about 5% by weight to about 95% by weight; and (ii) an alloying agent in the range of about 5% by weight to about 95% by weight. Yet another example of an alloyed composition includes (i) a composition comprising (i) a highly radiopaque material in the range of about 25% by weight to about 75% by weight; and (ii) an alloying agent in the range of about 25% by weight to about 75% by weight. Optionally, the highly radiopaque material may be present in the alloy in an amount by weight greater than about 50%, greater than about 75%, or greater than about 90%.

Member 22 in other embodiments of the present invention is made of a metallic material such as gold-plated silver. As indicated above, silver has a high mass x-ray absorption coefficient, and silver radiopaque endodontic marking tools display a very high contrast with respect to the surrounding dental material. However, silver is not chemically inert under autoclave conditions. To be able to sterilize silver embodiments according to the present invention, the preferred metallic material comprises a gold-coated silver core that can be subjected to autoclave conditions. The gold plating provides corrosion protection. Although still exhibiting a good compromise between flexibility and stiffness, and displaying high contrast visibility upon exposure to x-rays in a root canal, gold-plated silver embodiments are more expensive than tungsten embodiments. However, the additional cost can be offset because gold-plated silver embodiments can be sterilized under autoclave conditions and re-used.

The radiopaque endodontic marking tool may have any configuration that is suitable for placement within a root canal for detection by a radiographic instrument in order to determine the size of the root canal and to determine if the size of a tool to be used within the root canal is appropriate. Such tools have an elongate member with a distal insertion end opposite a proximal end that is adapted for insertion within a root canal and are at least partially formed from highly radiopaque material.

As indicated above, tool 20 is shown in FIG. 2 having a radiopaque elongate member 22 sheathed within handle 28 such that a portion of member 22 extends from a distal stop end 29 of handle 28 with sufficient length to extend into a root canal. The radiopaque member 22 is preferably substantially straight, and flexible enough to negotiate the angles of the root canal. However, it will be appreciated that radiopaque member 22 may be angled at its proximal end such that the radiopaque member is convenient to manipulate. The optional handle is designed for convenient manipulation of the measuring instrument.

Figure 3:
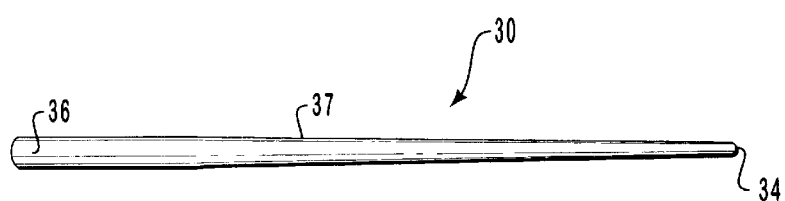
FIG. 3 is a top view of another embodiment of an endodontic marking tool 30 of the present invention.

In one embodiment shown in FIG. 3, the dental tool comprises only a radiopaque elongate member 30. Elongate member 30 has a proximal end 36 which is used an integral handle. Use of an integral handle may enable radiopaque elongate member 30 to be manufactured less expensively than dental tool 20. Like the surface 27 of elongate member 22, elongate member 30 has a relatively smooth surface 37. The elongate member preferably has such a smooth surface as opposed to a surface configured to abrade or cut the root canal surfaces, such as that shown in FIG. 5, as it is often easier to insert an elongate member to the desired position within the root canal that creates less friction. However, as discussed below, it may be useful in some embodiments to have some abrasive ability to move beyond certain obstructions.

Figure 4:
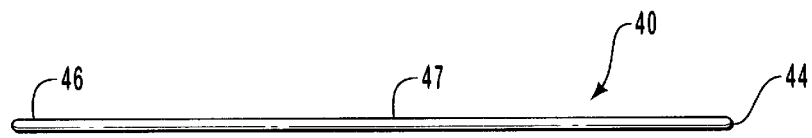
FIG. 4 is a top view of yet another embodiment of an endodontic marking tool 40 of the present invention.

FIG. 4 depicts another embodiment of a dental tool comprising a radiopaque elongate member 40 in the form of a slender rod or wire. Like radiopaque member 30, radiopaque member 40 has an integral handle and a smooth surface 47. The respective distal insertion ends 34 and 44 of radiopaque member 30 and radiopaque member 40 have the same diameter. Note, however, that while the diameter of radiopaque elongate member 40 remains constant along its length, the diameter of radiopaque elongate member 30 tapers in diameter from its proximal end or integral handle 36 to its distal insertion end 34. The constant diameter of elongate member 40 enable elongate member 30 to be manufactured less expensively than radiopaque elongate member 30. However, the tapered configuration of elongate member 22 and elongate member 30 provides greater rigidity at the proximal end so that the elongate member can be more easily directed as desired.

The cost for the elongate member may be reduced by utilizing a hollow elongate member, however, the elongate member is preferably solid. The cost for the elongate member may be further reduced by utilizing a material other than a highly radiopaque material that is less expensive than the highly radiopaque materials to form the elongate member and then coating the elongate member with a highly radiopaque material. However, as indicated above, the elongate member is preferably formed entirely from a highly radiopaque material or a highly radiopaque material that is alloyed, mixed or combined with another material so that the resulting material is still adequately radiopaque for high contrast. For example, the highly radiopaque material may include a material such as barium sulfate mixed in another material such as a plastic. The highly radiopaque material used in the elongate member may be coated or uncoated, however, the highly radiopaque material is preferably not coated. The elongate member is preferably not hollow as a solid elongate member creates a better radiographic image.

Figure 5:
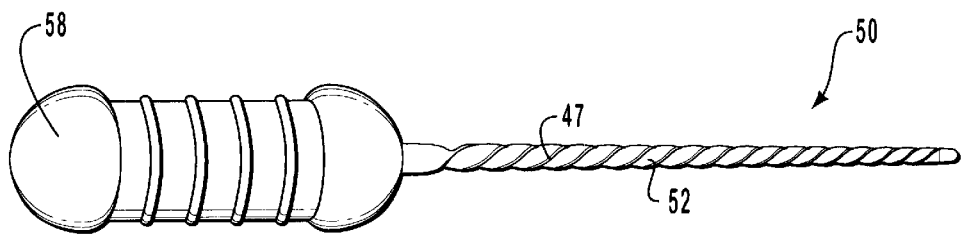
FIG. 5 is a top view of an additional embodiment of an endodontic marking tool 50 of the present invention.

Optionally, the tool of the present invention may comprise a radiopaque elongate member having cutting capabilities such as a bit or file. FIG. 5 depicts a tool at 50 that has radiopaque elongate member 52 configured like a file. Radiopaque elongate member 52 extends from a handle 58 like radiopaque elongate member 22 however elongate member 52 has fluting 57 on its surface.

The fluting 57 is an example of a surface on an elongate member designed to enhance manipulation of the surfaces of a root canal, such as by having cutting flutes, knurls, grooves, notches, or ridges, for example. Other examples of suitable file configurations are disclosed in U.S. Patent Application entitled Abrasive Coated Endodontic Instruments and Related Systems and Methods for the Anatomical, Sectional and Progressive Corono-Apical Preparation of Root Canals, filed Mar. 27, 2000, Ser. No. 09/536,284, which is incorporated herein in its entirety by reference. The flutes or other abrasive surface of the instrument can be designed to be used for abrading with varying aggressiveness. For example, the surface may be sandblasted or etched to have a surface that cuts less aggressively than fluting 57 such as the surface shown in FIG. 6 of elongate member 22'.

Elongate members having fluted files or other abrasive surfaces can be frictionally pressed against root canal surfaces in an abrading manner. However, the elongate member needs to have a certain balance of rigidity and flexibility or ductility in order for an elongate member configured for abrasive action against the surfaces of the root canal to be urged against the root canal surfaces.

The elongate members (e.g., members 22, 30, 40, and 52) disclosed herein are each examples of elongate means for positioning within a root canal of a tooth for radiographic viewing. Each handle disclosed herein (e.g., handles 28, 36, 46, and 58) is an example of a handle means for grasping and moving the elongate means.

The handle may be integrally coupled to the elongate member or nonintegrally coupled thereto. Thus, in one embodiment, the endodontic tool of the present invention comprises (i) an elongate means, e.g., shaft portion 30; and (ii) a handle means, e.g., handle portion 36, for grasping and moving the elongate means. A handle such as handle 28 is typically nonintegral and fixedly attached however it may also be coupled integrally to member 22.

Figure 6:
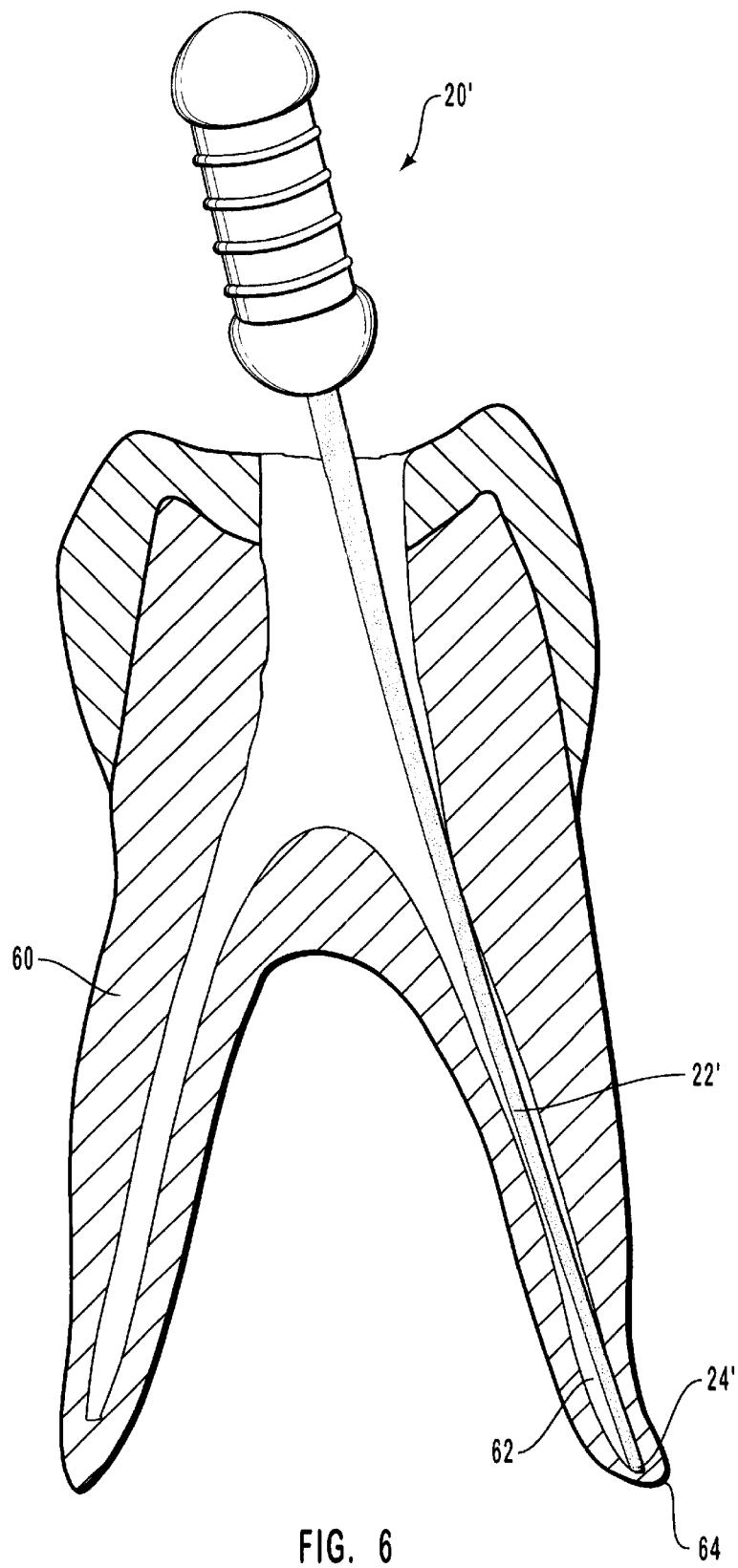
FIG. 6 is a view of a cross section of a tooth which has undergone a root canal procedure and has received the tool of FIG. 2 within a root canal thereof preparatory to radiography of the tooth and tool to determine the distance between the tip of the tool and the apex of the root canal.

FIG. 6 demonstrates an example of a modified version of dental tool 20 of FIG. 2 identified as 20' being placed within a root canal 62 of a partially cleaned tooth 60. As mentioned above, the elongate member 22' of tool 20' has a surface adapted for abrading root canal surfaces that is configured for less aggresive abrasion than is an elongate member such as elongate member 52 that has fluting 57 on its surface. As shown, elongate member 22' is disposed in root canal 62 so that a x-ray image or radiograph may be made. Once a radiograph is taken of tooth 60 and elongate member 22' of dental tool 20', it will be possible for the practitioner to determine the distance between the end 24' of dental tool 20' and the apex 64 of root canal 62, thereby determining any distance which the practitioner must further bore or clean.

According to one method of use, an initial radiographic image of a tooth is made and the depth of the root canals of the tooth are estimated. Then the pulp chamber of the tooth is opened. Next, at least a large part of the pulp in the pulp chamber and canals is removed. Elongate member 22 of tool 20 may then be placed into the root canal. A radiograph, such as an x-ray is then made of the tooth and tool 20. The distance between the end 24 of dental tool 20 and the apex 64 of the tooth 60 is determined, after which the practitioner can determine if further cleaning is required.

The radiographic tool such as tool 20 may be employed in a variety of different radiographic procedures used to determine the length of a root canal. For example, in addition to an initial measurement before actually cleaning the root canal, dental tool 20 or the other radiographic dental tools disclosed herein may be used after cleaning various portions of the root canal. Also the dental tool may be utilized to ensure that the apex has been reached and cleaned by inserting the root canal at the end of a root canal procedure. So the elongate member may be used at any point during a root canal procedure and in any manner required in dentistry.

With respect to the size of the desired dental tools, the tools can be generally the same diameter and length as files or other tools typically used in endodontic procedures, for example, or other sizes which fit into a root canal and allow negotiation therein. The tools may be tapered such as in the shape of a standard ISO tapered file, for example. However, the dental tools are preferably relatively thin. Although, the elongate member may have any suitable diameter along its length that enables it to extend throughout a root canal, the preferred diameter at the distal insertion end is typically in a range from about 0.025 mm to about 0.5 mm. The diameter is more typically in a range from about 0.1 mm to about 0.2 mm, and most typically about 0.15 mm. Note that the distal insertion end is preferably rounded so that it has sufficient thickness to be easily seen.

EXAMPLES OF THE INVENTION

As mentioned above, the highly radiopaque materials of the present invention may be employed in pure forms or as combinations such as alloys. Examples of such pure highly radiopaque materials which are especially useful for the formation of the elongate member include gold, platinum, palladium, silver, tungsten, and the like. Such materials are highly radiopaque and can be formed into elongate members having sufficient rigidity and ductility to extend to a desired location within a root canal of a tooth. The elongate member may also be manufactured with a metallic material formed by combining a highly radiopaque material and an alloy so that the alloyed radiopaque metallic material resulting therefrom has a mass x-ray absorption coefficient that is no less than about 1.5, about 1.5 or greater than 1.5. The following examples provide hypothetical compositions for forming elongate members of radiopaque instruments from such highly radiopaque materials.

Example 1

In this example, an elongate member configured to be inserted within a root canal of a tooth is formed from the following formula:

| Component | Percent by Weight |
|---|---|
| Gold | 100% |

Such a tool would be expected to be highly radiopaque and to have sufficient rigidity and ductility to extend to a desired location within a root canal of a tooth. Gold is highly radiopaque, has good corrosion resistance, has a high density, and is ductile, but is generally high in cost.

Example 2

In this example, an elongate member configured to be inserted within a root canal of a tooth is formed from the following formula:

| Component | Percent by Weight |
|---|---|
| Platinum | 100% |

Such a tool would be expected to be highly radiopaque and to have sufficient rigidity and ductility to extend to a desired location within a root canal of a tooth. Platinum has a slightly lower mass x-ray absorption coefficient than gold. Platinum has a high density (slightly higher in density than gold). Platinum is generally high in cost, often costing more than gold. Platinum has good corrosion resistance and is ductile.

Example 3

In this example, an elongate member configured to be inserted within a root canal of a tooth is formed from the following formula:

| Component | Percent by Weight |
| --- | --- |
| Palladium | 100% |

Such a tool would be expected to be highly radiopaque and to have sufficient rigidity and ductility to extend to a desired location within a root canal of a tooth. Palladium is highly radiopaque, its mass x-ray absorption coefficient is much higher than gold and generally costs less than gold. Palladium also has good corrosion resistance and is ductile.

Example 4

In this example, an elongate member configured to be inserted within a root canal of a tooth is formed from the following formula:

| Component | Percent by Weight |
| --- | --- |
| Tungsten | 100% |

Such a tool would be expected to be highly radiopaque and to have sufficient rigidity and ductility to extend to a desired location within a root canal of a tooth. Tungsten has a mass x-ray absorption than is less than that of gold, platinum, palladium and silver, however, tungsten is also generally less expensive than these highly radiopaque metals. Tungsten has good corrosion resistance and is ductile.

Example 5

In this example, an elongate member configured to be inserted within a root canal of a tooth is formed from an alloy having the following formula:

| Component | Percent by Weight of the Alloy |
| --- | --- |
| Gold | 75% |
| Platinum | 25% |

Such an alloyed tool would be expected to be highly radiopaque, to have good corrosion resistance, and to have sufficient rigidity and ductility to extend to a desired location within a root canal of a tooth. Such a tool would also be expected to be generally high in cost.

Example 6

In this example, an elongate member configured to be inserted within a root canal of a tooth is formed from an alloy having the following formula:

| Component | Percent by Weight of the Alloy |
| --- | --- |
| Platinum | 75% |
| Gold | 25% |

Such an alloyed tool would be expected to be highly radiopaque, to have good corrosion resistance, and to have sufficient rigidity and ductility to extend to a desired location within a root canal of a tooth. Such a tool would also be expected to be generally high in cost.

Example 7

In this example, an elongate member configured to be inserted within a root canal of a tooth is formed from an alloy having the following formula:

| Component | Percent by Weight of the Alloy |
| --- | --- |
| Palladium | 75% |
| Gold | 25% |

Such an alloyed tool would be expected to be highly radiopaque, to have good corrosion resistance, and to have sufficient rigidity and ductility to extend to a desired location within a root canal of a tooth. Such a tool would also be expected to be relatively low in cost by comparison to the alloyed materials of examples 5 and 6.

Example 8

In this example, an elongate member configured to be inserted within a root canal of a tooth is formed from an alloy having the following formula:

| Component | Percent by Weight of the Alloy |
| --- | --- |
| Palladium | 75% |
| Platinum | 25% |

Such an alloyed tool would be expected to be highly radiopaque, to have good corrosion resistance, and to have sufficient rigidity and ductility to extend to a desired location within a root canal of a tooth. Such a tool would also be expected to be relatively low in cost by comparison to the alloyed materials of examples 5 and 6.

Example 9

In this example, an elongate member configured to be inserted within a root canal of a tooth is formed by gold plating a silver core. Such a tool would be expected to be highly radiopaque, to have good corrosion resistance, and to have sufficient rigidity and ductility to extend to a desired location within a root canal of a tooth.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed and desired to be secured by United States Letters Patent is:

1. A radiopaque endodontic tool configured for placement within a root canal for detection by a radiographic instrument, the tool comprising:
   elongate means for positioning within a root canal of a tooth for radiographic viewing, the elongate means having
      a distal insertion end; and
      a proximal end; and
   handle means for grasping and moving the elongate means;
   wherein the elongate means includes a highly radiopaque material that is non-toxic and that includes an element selected from the group consisting of gold, platinum, palladium, silver, and tungsten;
   wherein the elongate means has a mass x-ray absorption coefficient that is no less than about 1.5;
   wherein the elongate means has a surface adapted for abrading root canal surfaces;
   wherein the elongate means has sufficient rigidity and is sufficiently ductile to extend to a desired location within a root canal of a tooth; and
   wherein the elongate means has a length and outer diameter that enables the elongate means to extend throughout a root canal and to reach an apex of the root canal of a tooth.

2. An endodontic tool as recited in claim 1, wherein the highly radiopaque material is a highly radiopaque metallic material and wherein the highly radiopaque metallic material is alloyed with an alloying agent.

3. An endodontic tool as recited in claim 1, wherein the highly radiopaque material is a highly radiopaque metallic material and wherein the highly radiopaque metallic material is alloyed with an alloying agent which is different from the highly radiopaque metallic material and is selected from the group consisting of copper, chromium, iridium, iron, gold, nickel, osmium, platinum, palladium, rhenium, rhodium, ruthenium, silver, titanium and tungsten.

4. An endodontic tool as recited in claim 1, wherein the highly radiopaque material is a metallic material plated onto another metallic material.

5. An endodontic tool as recited in claim 1, wherein the elongate means is autoclavable, non-corrosive, and non-oxidizing.

6. An endodontic tool as recited in claim 1, wherein the handle means is integrally coupled to the elongate means.

7. An endodontic tool as recited in claim 1, wherein the handle means is nonintegrally coupled to the elongate means.

8. An endodontic tool as recited in claim 1, wherein the elongate means has a mass x-ray absorption coefficient that is at least about 3.

9. An endodontic tool as recited in claim 1, wherein the elongate means has a mass x-ray absorption coefficient that is at least about 3.5.

10. A radiopaque endodontic tool configured for placement within a root canal for detection by a radiographic instrument, the tool comprising:
    an elongate member having a distal insertion end opposite a proximal end;
    wherein the elongate member includes a highly radiopaque material that is non-toxic and that includes an element selected from the group consisting of gold, platinum, palladium, silver, and tungsten;
    wherein the elongate member has a mass x-ray absorption coefficient that is no less than about 1.5;
    wherein the elongate member has a surface adapted for abrading root canal surfaces;
    wherein the elongate member has sufficient rigidity and ductility to extend to a desired location within a root canal of a tooth; and
    wherein the elongate member has a length and outer diameter that enables the elongate member to extend throughout a root canal and to reach an apex of the root canal of a tooth.

11. An endodontic tool as recited in claim 10, wherein the highly radiopaque material is alloyed with an alloying agent.

12. An endodontic tool as recited in claim 10, wherein the highly radiopaque material is a highly radiopaque metallic material; and
    wherein the highly radiopaque metallic material is alloyed with an alloying agent which is different from the highly radiopaque metallic material and is selected from the group consisting of copper, chromium, iridium, iron, gold, nickel, osmium, platinum, palladium, rhenium, rhodium, ruthenium, silver, titanium, tungsten.

13. An endodontic tool as recited in claim 10, wherein the highly radiopaque material is a metallic material plated onto another metallic material.

14. An endodontic tool as recited in claim 10, wherein the elongate member is autoclavable, non-corrosive, and non-oxidizing.

15. An endodontic tool as recited in claim 10, wherein the endodontic tool includes a handle integrally coupled to the elongate member.

16. An endodontic tool as recited in claim 10, wherein the endodontic tool includes a handle nonintegrally coupled to the elongate member.

17. An endodontic tool as recited in claim 10, wherein the elongate member has a mass x-ray absorption coefficient that is at least about 3.

18. An endodontic tool as recited in claim 10, wherein the elongate member has a mass x-ray absorption coefficient that is at least about 3.5.

19. A radiopaque endodontic tool configured for placement within a root canal for detection by a radiographic instrument, the tool comprising:
    an elongate member having a distal insertion end opposite a proximal end;
    wherein the elongate mengate member includes a non-toxic highly radiopaque material that includes an element selected from the group consisting of gold, platinum, palladium, silver and tungsten;
    wherein the elongate member has a mass x-ray absorption coefficient that is no less than about 2;
    wherein the elongate member has a surface adapted for abrading root canal surfaces;
    wherein the elongate member has sufficient rigidity and ductility to extend to a desired location within a root canal of a tooth; and
    wherein the elongate member has a length and outer diameter that enables the elongate member to extend throughout a root canal and to reach an apex of the root canal of a tooth.

20. A radiopaque endodontic tool configured for placement within a root canal for detection by a radiographic instrument, the tool comprising:
    an elongate member having a distal insertion end opposite a proximal end;
        wherein the elongate member includes sufficient tungsten such that the elongate member has a mass x-ray absorption coefficient that is no less than about 1.5;

wherein the elongate member has a surface adapted for abrading root canal surfaces;

wherein the elongate member has sufficient rigidity and ductility to extend to a desired location within a root canal of a tooth; and wherein the elongate member has a length and outer diameter that enables the elongate member to extend throughout a root canal and to reach an apex of the root canal of a tooth.

21. An endodontic tool as recited in claim 20, wherein the tungsten is alloyed with an alloying agent.

22. An endodontic tool as recited in claim 20, wherein the elongate member further comprises a highly radiopaque material other than tungsten.

23. A radiopaque endodontic tool configured for placement within a root canal for detection by a radiographic instrument, the tool comprising:

an elongate member having a distal insertion end opposite a proximal end;

wherein the elongate member comprises silver plated with gold;

wherein the elongate member has a x-ray absorption coefficient that is no less than about 1.5;

wherein the elongate member is non-toxic;

wherein the elongate member has a surface adapted for abrading root canal surfaces;

wherein the elongate member has sufficient rigidity and ductility to extend to a desired location within a root canal of a tooth; and wherein the elongate member has a length and outer diameter that enables the elongate member to be inserted within a root canal of a tooth.

24. A method for determining the length of a root canal, comprising:

(i) providing a radiopaque endodontic tool comprising an elongate member configured for placement within a root canal, the elongate member including a highly radiopaque material that is non-toxic and that includes an element selected from the group consisting of gold, platinum, palladium, silver, and tungsten, the elongate member having a mass x-ray absorption coefficient that is no less than about 1.5; the elongate member having a surface adapted for abrading root canal surfaces;

(ii) placing the elongate member within a root canal of a patient; and (iii) making a radiographic image of the root canal while the elongate member is disposed in the root canal.

25. A method as recited in claim 24, wherein the elongate member has a distal insertion end opposite a proximal end; and wherein the method further comprises measuring the distance between the distal end of the elongate member and an apex of the foot canal.

26. A method as recited in claim 24, wherein the elongate member has a mass x-ray absorption coefficient that is at least about 2.

27. A method as recited in claim 24, wherein the elongate member has a mass x-ray absorption coefficient that is at least about 3.

28. A method as recited in claim 24, wherein the elongate member has a mass x-ray absorption coefficient that is at least about 3.5.

* * * * *

UNITED STATES PATENT AND TRADEMARK OFFICE
CERTIFICATE OF CORRECTION

PATENT NO.    : 6,468,079 B1
DATED         : October 22, 2002
INVENTOR(S)   : Dan E. Fischer and Dan J. Bills It is certified that error appears in the above-identified patent and that said Letters Patent is hereby corrected as shown below:

Column 10,
Line 7, after "used" insert -- as --
Line 31, change "enable" to -- enables --

Column 15,
Line 39, after "titanium" insert -- , --

Column 16,
Line 21, before "tungsten" insert -- and --

Column 18,
Line 21, change "foot" to -- root --

Signed and Sealed this

Ninth Day of September, 2003

JAMES E. ROGAN
*Director of the United States Patent and Trademark Office*